United States Patent [19]

Rawlings et al.

[11] Patent Number: 5,472,698
[45] Date of Patent: Dec. 5, 1995

[54] COMPOSITION FOR ENHANCING LIPID PRODUCTION IN SKIN

[75] Inventors: Anthony V. Rawlings, Wyckoff; Kelly H. Zhang, Piscataway; Richard Kosturko, Nutley, all of N.J.

[73] Assignee: Elizabeth Arden Co., Division of Conopco, Inc., New York, N.Y.

[21] Appl. No.: 359,758

[22] Filed: Dec. 20, 1994

[51] Int. Cl.$^6$ .................................................... A61K 7/00
[52] U.S. Cl. .................... 424/401; 514/553; 514/558; 514/727; 514/844
[58] Field of Search ...................... 424/401; 514/727, 514/553, 558, 844

[56] References Cited

U.S. PATENT DOCUMENTS

| | | | |
|---|---|---|---|
| 4,016,287 | 4/1977 | Eberhardt et al. | 424/309 |
| 4,085,217 | 4/1978 | Kalopissis | 424/266 |
| 4,288,433 | 9/1981 | Koulbanis et al. | 424/232 |
| 4,411,886 | 10/1983 | Hostettler et al. | 424/70 |
| 4,468,519 | 8/1984 | Krapcho | 548/409 |
| 4,711,780 | 12/1987 | Fahim | 424/145 |
| 4,721,705 | 1/1988 | Shreuder | 514/54 |
| 4,724,140 | 2/1988 | Potin et al. | 424/70 |
| 4,743,442 | 5/1988 | Raaf et al. | 424/47 |
| 4,859,653 | 8/1989 | Morelle et al. | 514/2 |
| 4,885,157 | 12/1989 | Fiaschetti | 424/59 |
| 4,950,688 | 8/1990 | Bowser et al. | 514/847 |
| 4,981,845 | 1/1991 | Pereira | 514/557 |
| 4,985,547 | 1/1991 | Yano et al. | 536/4.1 |
| 5,028,416 | 7/1991 | Yano et al. | 424/59 |
| 5,047,249 | 9/1991 | Rothman et al. | 424/543 |
| 5,071,971 | 12/1991 | Yano et al. | 536/4.1 |
| 5,091,171 | 2/1992 | Yu et al. | 424/642 |
| 5,135,741 | 8/1992 | Park | 424/66 |
| 5,141,741 | 8/1992 | Ishida et al. | 424/59 |
| 5,154,916 | 10/1992 | Arraudeau | 424/63 |
| 5,175,321 | 12/1992 | Ohashi et al. | 554/63 |
| 5,226,914 | 7/1993 | Caplan | 623/16 |
| 5,294,444 | 3/1994 | Nakamura et al. | 424/401 |
| 5,296,500 | 3/1994 | Hillebrand | 514/562 |

FOREIGN PATENT DOCUMENTS

| | | |
|---|---|---|
| 0219455 | 4/1987 | European Pat. Off. . |
| 0280606 | 8/1988 | European Pat. Off. . |
| 0440398 | 8/1991 | European Pat. Off. . |
| 2651129 | 1/1991 | France . |
| 60124 | 9/1990 | Hungary . |
| 0120611 | 9/1981 | Japan . |
| 2180153 | 3/1987 | United Kingdom . |
| 93/04669 | 3/1993 | WIPO . |
| 93/10755 | 6/1993 | WIPO . |

OTHER PUBLICATIONS

Kahn, Guinter et al., "Ultraviolet Light Protection by Several New Compounds", Arch. Dermatol., vol. 109, Apr. 1974, pp. 510–517.
Abstract of JP 5339140 Apr. 1994.
Gavish, D. et al., "Lipoprotein(a) reduction by N-acetylcysteine", The Lancet, vol. 337, Jan. 26, 1991, pp. 203–204.
Derwent Abstract of Japanese Patent No. 131538, Jun. 1985.
Holleran, Walter M., et al., "Sphingolipids are Required for Mammalian Epidermal Barrier Function", The Journal of Clinical Investigation, Inc., vol. 88, Oct. 1991, pp. 1338–1345.
Holleran, W. M., et al., "Serine–palmitoyl Transferase Activity in Cultured Human Keratinocytes", Journal of Lipid Research, vol. 31, 1990, pp. 1655–1661.

Primary Examiner—Gollamudi S. Kishore
Attorney, Agent, or Firm—Rimma Mitelman

[57] ABSTRACT

Skin treatment compositions for the enhancement of lipid production in the skin. Compositions contain a thiol, or an S-ester, in combination with L-serine or N-acetyl-L-serine.

10 Claims, No Drawings

COMPOSITION FOR ENHANCING LIPID PRODUCTION IN SKIN

FIELD OF THE INVENTION

The invention relates to skin treatment compositions containing L-serine or N-acetyl-L-serine in combination with a thiol or an S-ester, and the use of the compositions for enhancing lipid production in mammalian skin.

BACKGROUND OF THE INVENTION

Layers of lipids in stratum corneum of the skin form a "water barrier" which prevents water loss from the skin. Known classes of stratum corneum lipids include sphingolipids, free fatty acids, sterols and sterol esters, and phospholipids, with sphingolipids being a major component. Sphingolipids, in turn, consist of four major classes of lipids: glycosphingolipids, ceramides, sphingomyelin and total sphingoid base. Ceramides and other sphingolipids play a major role in promoting cell differentiation and, thus, preventing, reducing, or eliminating skin dryness and wrinkles. Although several species of natural ceramides have been identified, these ceramides must be obtained through a lengthy process involving the extraction of ceramides from natural sources. Thus, the availability of natural ceramides is limited and their cost is very high. Several analogs of natural ceramides, known as pseudoceramides, have been synthesized. Pseudoceramides look similar but are not identical to ceramides. Unfortunately, pseudoceramides are still expensive, albeit not as expensive as natural ceramides.

Recent work has shown the ability of cultured keratinocytes to synthesize sphingolipids. Due to the high cost of natural or synthetic sphingolipids, cosmetic compositions which can enhance production of sphingolipids are desirable, in order to minimize or eliminate the need for exogenous application of sphingolipids.

Skin care compositions are known, which include some of the thiol compounds disclosed herein. For example, some thiol compounds have been employed in skin treatment compositions as anti-oxidants. See EP 0 440 398 (Johnson and Johnson) and EP 0 280 606 (L'Oreal). Fahim, U.S. Pat. No. 4,711,780 discloses a composition for epithelial regeneration containing vitamin C, a zinc salt and a sulfur amino acid, such as cystine or cysteine, or glutathione. Schreuder, U.S. Pat. 4,721,705 discloses the use of N-acyl cysteine, or S-acyl-cysteine in compositions for treating sun eczema or dishydrosis of skin. Several thiol compounds have been identified as effective UV light screening agents. See Kahn, Guinter et al. "Ultraviolet Light Protection by Several New Compounds", *Arch. Dermatol.*, Vol. 109, (April 1974) pp. 510–517, and WO 9404129 (Beiersdorf). Hillebrand, U.S. Pat. No. 5,296,500, discloses compositions containing N-acetyl-L-cysteine or derivatives thereof. The compositions are said to efface and prevent wrinkles in mammalian skin.

JP 5339140 discloses a skin cosmetic material containing a mucin and aminoacid, (e.g., serine). The compositions are said to have good moisture retention and improve the wetness of skin. Raaf, U.S. Pat. No. 4,743,442 and Pereira, U.S. Pat. No. 4,981,845 disclose skin care compositions which may contain amino acids, such as serine, cystine, cysteine. Ishida, U.S. Pat. No. 5,141,741, discloses anti-sunburn skin care compositions which may contain vitamins and amino acids as optional ingredients. α-lipoic acid is mentioned among suitable vitamins; serine and cystine are mentioned among suitable amino acids. Park, U.S. Pat. No. 5,135,741, discloses an anti-perspirant composition containing a compound having a basic nitrogen function, e.g., thiourea or amino acids such as serine.

The art discussed above does not address the need for increasing sphingolipid production in skin and does not envision skin treatment compositions based on a lipid production enhancing system of a thiol or an S-ester or a disulfide and L-serine or N-acetyl-L-serine according to the present invention.

Accordingly, it is an object of the present invention to provide skin treatment compositions for increasing sphingolipid production in mammalian skin.

It is another object of the invention to provide a composition for improving skin condition by improving water barrier performance.

It is another object of the invention to provide a method for treating or preventing the appearance of wrinkled, flaky, aged, photodamaged skin or skin disorders.

These and other objects of the invention will become more apparent from the detailed description and examples that follow.

SUMMARY OF THE INVENTION

The above objects are attained by the present invention which includes, in part, a skin treatment composition containing:

(i) from about 0.0001% to about 50% of an ingredient selected from the group consisting of L-serine, N-acetyl-L-serine and mixtures thereof;

(ii) from about 0.0001% to about 50% of an ingredient selected from the group consisting of a thiol, an S-ester, a disulfide and mixtures thereof; and (iii) a cosmetically acceptable vehicle.

The invention is based, in part, on the discovery that a specific combination of actives enhances sphingolipid production in skin. Although some of the actives taught herein enhance sphingolipid production even when used alone, a combination of actives according to the present invention results in a synergistic increase in sphingolipid production.

In the preferred embodiment of the invention, inventive compositions include an alpha hydroxy acid, and/or dicarboxylic alpha hydroxy acids, and most preferably an L-stereoform thereof.

A further advantage of the present compositions is that lower levels of ceramides and/or other sphingolipids may be included in the composition containing sphingolipid production enhancing system of the present invention to equal the performance of a similar formulation without the inventive system in order to minimize the cost of compositions.

The present invention also includes a method of improving or preventing the appearance of dry, flaky, wrinkled, aged, photodamaged skin and treating skin disorders, which method includes applying to the skin an inventive composition.

Compositions of the invention are intended for topical application to mammalian skin which is already in dry, flaky, wrinkled, aged, photodamaged condition or which suffers from a skin disorder, or, in the alternative, the inventive compositions may be applied prophylactically to normal healthy skin to prevent or reduce dryness and the deteriorative changes.

DETAILED DESCRIPTION OF THE INVENTION

The first essential ingredient of the inventive composition is selected from the group consisting of an L-serine, an N-acetyl-L-serine, and mixtures thereof.

The total amount of L-serine and/or N-acetyl-L-serine in the inventive compositions ranges from 0.0001% to 50%, preferably from 0.01% to 20%, and most preferably from 1% to 20% by weight of the composition, in order to attain maximum performance at optimal cost.

The second essential ingredient of inventive compositions is a co-active ingredient selected from the group consisting of a thiol, an S-ester, a disulfide and mixtures thereof.

The term "thiol" as employed herein means a compound containing at least one sulfhydryl group (—SH), other than the amino acid cysteine. The term "S-ester" as employed herein means a compound containing at least one group of formula

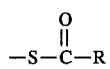

wherein R is an alkyl, hydroxyalkyl, alkenyl, or an aryl group, preferably containing from 2 to 16 carbon atoms.

The term "disulfide" means a compound of general formula:

wherein R is as defined above.

Examples of suitable thiol compounds include but are not limited to cystamine dihydrochloride cysteamine, N-acetyl-cysteamine, N-acetyl-L-cysteine, DL-6,8-thioctic acid (also known as DLα-lipoic acid) or salts thereof, thioacetamide, thioacetanilide, o-thiocresol, m-thiocresol, p-thiocresol, DL-6-thioctic acid, DL-6-thioctic amide, thiodiacetic acid, thiodiglycolic acid, thiosalicyclic acid, thiogalactoside, thiodiglucoside, 3,3'-thiodipropionic acid, thioglycolic acid, 1-thio-β-D-glucose, thiourea, pantetheine, dithioerythritol, 1,4-dithio-L-threitol mercaptoacetic acid, 2-mercaptobenzimidazole, 2-mercaptobenzothiazole, 2-mercaptobenzoxazole, 2-mercapto-2-butanol, 2-mercaptoethanol, 2-mercapto-ethyl sulfide, 2-mercapto-imidazole, 2-mercaptomenthone, 2-mercaptonicotinic acid, 2-mercapto-5-nitro-benzimidazole, 3-mercapto-1-propanediol (also known as 1-thioglycerol), 2-mercaptopropionic acid (also known as thiolactic acid), 3-mercaptopropionic acid, N-(2-mercaptopropionyl)glycine, 2-mercaptopyrimidine, mercaptosuccinic acid, 2,3-dimercapto-1-propanesulfonic acid (DMPS), 2,3-dimercapto-1-propanol (BAL), 2,3,-dimercapto-1-propanol tributyrate, meso-2,3-dimercaptosuccinic acid, 3,4-dimercaptotoluene.

Preferably, a thiol compound is N-acetyl-L-cysteine or α-lipoic acid because these two compounds are directly involved in natural skin-specific antioxidant pathways.

Suitable examples of compounds containing an S-ester group include but are not limited to cysteine S-esters (e.g., S-acetamidomethyl-L-cysteine, (S)-2-aminoethyl-L-cysteine, S-benzyl-L-cysteine, S-benzyl-L-cysteine ethyl ester, S-benzyl-L-cysteine methyl ester, S-t-butylmercapto-L-cysteine, S-carbamyl-L-cysteine, S-ethyl-L-cysteine, S-methyl-L-cysteine, S-lactoyl-cysteine, S-hydroxycaproyl-cysteine, S-adenosylmethionine, coenzyme A derivatives (e.g., N,S-Diacetyl-β-mercaptoethylamine), S-esters of glutathione (e.g., S-lactoyl glutathione), S-butylglutathione, S-methyl-glutathione, S-decylglutathione, S-ethylgluta-thione, S-heptylglutathione, S-hexylglutathione, S-nonylglutathione, S-octyl-glutathione, S-pentylglutathione, S-propylglutathione.

Examples of suitable disulfides include but are not limited to N-acyl or hydroxyacyl derivatives of cystine and 2,2'-dithiosalicylic acid.

Preferably, a co-active ingredient employed herein is an S-ester or a thiol compound rather than a disulfide, in order to attain better penetration into skin and to eliminate or minimize an unpleasant odor.

A thiol and/or an S-ester and/or a disulfide is employed in the inventive compositions in the amount ranging from about 0.0001% to about 50%. The precise amount will depend on the particular thiol or an S-ester included in the inventive compositions. Preferably, the amount is in the range of from 0.01% to 20% by weight of the composition, most preferably in the range of from 0.1% to 5% to attain maximum performance at optimal cost.

In the first preferred embodiment, the inventive compositions contain N-acetyl-serine in combination with lipoic acid. In the second preferred embodiment, the inventive compositions contain serine or N-acetyl-serine in combination with N-acetyl-cysteine in order to attain maximum benefit and to minimize or substantially reduce the unpleasant odor.

The composition according to the invention also comprises a cosmetically acceptable vehicle to act as a dilutant, dispersant or carrier for the active components in the composition, so as to facilitate their distribution when the composition is applied to the skin, hair and/or nails.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

The cosmetically acceptable vehicle will usually form from 5 to 99.9%, preferably from 25 to 80% by weight of the emulsion, and can, in the absence of other cosmetic adjuncts, form the balance of the composition.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents, skin conditioning and moisturing agents, anti-dandruff agents, hair conditioners and hair growth stimulants.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

A preferred optional active ingredient to be included in the inventive composition are ceramides which play an important role in the production and maintenance of the water permeability barrier of the skin. Suitable ceramides and synthetic analogues thereof are disclosed in European Patent Application No. 534 286, European Patent Application No. 282 816, European Patent Application No. 227 994, U.S. Pat. Nos. 5,175,321, 4,985,547, 5,028,416, 5,071,971, Japanese Patent Application No. 63192703, U.S. Pat. Nos. 4,468,519, and 4,950,688, all of which are incorporated by reference herein. Ceramides or their synthetic analogues may be present in the inventive compositions at a level of from about 0.00001% to about 5%, preferably from about 0.000% to about 1%, optimally from about 0.01% to 0.5%.

Another preferred optional ingredient is selected from essential fatty acids (EFAs), i.e., those fatty acids which are essential for the plasma membrane formation of all cells. In keratinocytes EFA deficiency makes cells hyperproliferative. Supplementation of EFA corrects this. EFAs also enhance lipid production of epidermis and provide lipids for the barrier formation of the epidermis. The essential fatty acids are preferably chosen from linoleic acid, γ-linolenic acid, homo-γ-linolenic aid, columbinic acid, eicosa-(n-6,9, 13)-trienoic acid, arachidonic acid, γ-linolenic acid, timnodonic acid, hexaenoic acid and mixtures thereof.

The inventive compositions preferably include hydroxy-acids. Hydroxyacids enhance proliferation and increase ceramide production in keratinocytes, increase epidermal thickness, and increase desquamation of normal skin resulting in smoother, younger looking skin.

The hydroxy acid can be chosen from α-hydroxy acids, β-hydroxyacids, other hydroxycarboxylic acids (e.g., dihydroxycarboxylic acid, hydroxydicarboxylic, hydroxytricarboxylic) and mixtures thereof or combination of their stereoisomers (DL, D or L).

Preferably the hydroxy acid (ii) is chosen from α-hydroxy acids having the general structure (13):

(13)

where

M is H— or $CH_3(C_fH_g)_h$—, f is an integer of from 1 to 27, g is an integer of from 2 to 54, and his 0 or 1.

Even more preferably the hydroxy acid is chosen from 2-hydroxyoctanoic acid, hydroxylauric, lactic acid, and glycolic acid, and mixtures thereof. When stereo isomers exist, L-isomer is most preferred.

The keto acids can be chosen from α-keto acids, β-keto acids and mixtures thereof.

A particularly preferred α-keto acid is 2-keto octanoic acid.

Preferably the amount of the hydroxy acid component (ii) present in the composition according to the invention is from 0.01 to 20%, more preferably from 0.05 to 10% and most preferably from 0.1 to 3% by weight.

Surfactants, which are also sometimes designated as emulsifiers, may be incorporated into the cosmetic compositions of the present invention. Surfactants can comprise anywhere from about 0.5% to about 30%, preferably from about 1% to about 15% by weight of the total composition. Surfactants may be cationic, nonionic, anionic, or amphoteric in nature and combinations thereof may be employed.

Illustrative of the nonionic surfactants are alkoxylated compounds based upon fatty alcohols, fatty acids and sorbitan. These materials are available, for instance, from the Shell Chemical Company under the "Neodol" designation. Copolymers of polyoxypropylene-polyoxyethylene, available under the Pluronic trademark sold by the BASF Corporation, are sometimes also useful. Alkyl polyglycosides available from the Henkel Corporation similarly can be utilized for the purposes of this invention.

Anionic-type surfactants may include fatty acid soaps, sodium lauryl sulphate, sodium lauryl ether sulphate, alkyl benzene sulphonate, mono and/or dialkyl phosphates and sodium fatty acyl isethionate.

Amphoteric surfactants include such materials as dialkylamine oxide and various types of betaines (such as cocoamido propyl betaine).

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust bean gum. Under certain circumstances the thickening function may be accomplished by a material also serving as a silicone or emollient. For instance, silicone gums in excess of 10 centistokes and esters such as glycerol stearate have dual functionality.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds.

Particularly preferred preservatives of this invention are methyl paraben, propyl paraben, imidazolidinyl urea, sodium dehydroxyacetate and benzyl alcohol. Preservatives will usually be employed in amounts ranging from about 0.5% to 2% by weight of the composition.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

Use of the Composition

The composition according to the invention is intended primarily as a product for topical application to human skin, especially as an agent for reducing the permeability to water of the skin, particularly when the skin is dry or damaged, in order to reduce moisture loss and generally to enhance the quality and flexibility of skin. The composition can also be applied to hair and nails.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

EXAMPLES

Materials: N-acetyl-L-cysteine, thioglycerin, thiosalicylic acid, α-lipoic acid N-acetyl-L-serine and L-serine were purchased from Sigma Chemical Co. St. Louis, Mo. Keratinocyte culture medium KGM and L-serine-free-KGM were from Clonetics, San Diego, Calif. Dulbecco's Modified Eagle Media (DMEM) are from GIBCO BRL, Grand Island, N.Y. a $^3$H-serine is from Amersham Corporation, Arlington Heights, Ill. $^{14}$C-acetate are from DuPont NEN Research Products, Boston, Mass.

EXAMPLE 1

Stimulation of Ceramide Production in Human keratinocytes by Thiols and L-Serine To study the effects of thiols and L-serine on mass levels of ceramides production, human keratinocytes were cultured in L-serine-free-KGM (37° C, 5% $CO_2$) to 85–95% of confluence for 4 days and then supplemented with N-acetyl-L-cysteine ("NAC") or α-lipoic acid at the concentrations listed in Tables 1 and 2 below. Cells so treated were then incubated for 24 hours under the same conditions. Cells were then harvested for lipid analysis using the TLC method described below.

Lipid Extraction

Bligh-Dyer solution (chloroform:methanol:water= 2:4:1.6) was used to extract the epidermal lipids from the keratinocytes or the separated epidermis overnight (1 ml solution per 15 mg tissue) at −20° C. The cells or tissue were ground with a hand-held tissue homogenizer and shaken for 20 minutes on a Burrel wrist-action shaker at room temperature. Filtration is conducted through a Teflon syringe filter (Acrodisc CR, 0.451 μm). Tissue debris was spun down by centrifugation at 2000 rpm for 10 minutes. Supernatants were transferred to fresh test tubes and chloroform/water in a 1:1 ratio was added to the filtrates (4 ml of the solution per 7.6 ml of the filtrate). After shaking for 10 min, the mixture was centrifuged at 2000 rpm for 10 minutes and the aqueous phase (upper phase) was discarded.

Thin-Layer Chromatography

Aliquots of the lipid extract from each treatment were separated on precleaned, high-performance, thin-layer plates, 10×20 cm (LHP-KD, thin layer chromatography plates, Whatman, U.S.). Autospotter Linomat IV was used to apply the extracts on the TLC-plates. The plates were prewashed in a solvent system consisting of chloroform/methanol/glacial acetic acid (95/4.5/0.5 v/v) and developed in chambers saturated with the solvent system. All separations were carried out at room temperaure. Lipid standard mixtures (20 μg each) and ceramide standards were applied in parallel for identification and calibration purposes.

Ceramide standards used were ceramides III/IV of bovine brain from Sigma Chemical Co. (St Louis, Mo.), and ceramide I, a synthetic C-30 linoleic ceramide, from Cookson Chemicals, LTD. UK.

The plates were air-dried, sprayed with 10% copper sulfate, 8% phosphoric acid aqueous solution, and charred to a 180° C. Mass level quantification of individual ceramide species was performed by densitometry, using a Model 620, VIDEO TLC densitometer, equipped with a computerized image analyzer.

The results that were obtained are summarized in Tables 1 and 2.

Each cell in the Tables below represents a mean of three experiments.

TABLE 1

Ceramide Production in the Presence of NAC/L-serine Combination

| Test | L-Serine Concentration (mM) | NAC Concentration (mM) | Ceramide Peak Area (arbitrary units) |
|---|---|---|---|
| A | 0 | 0 | 0 |
| B | 0.6 | 0 | 0 |
| C | 2.0 | 0 | 0 |
| D | 10.0 | 0 | 0 |
| E | 0 | 10.0 | 0 |
| F | 0.6 | 10.0 | 0.317* |
| G | 2.0 | 10.0 | 1.230* |
| H | 10.0 | 10.0 | 1.630* |

*Statistically significant increase over control (Test A)

TABLE 2

Ceramide Production in the Presence of α-Lipoic Acid/L-Serine Combination

| Test | Lipoic Acid Concentration (mM) | Serine Concentration (mM) | Ceramide Peak Area (arbitrary units) |
|---|---|---|---|
| A | 0 | 0 | 0 |
| B | 0 | 10 | 0 |
| C | 0.1 | 0 | 0 |
| D | 0.1 | 10 | 0.93* |

*Statistically significant increase over control (Test A)

The results in Table 1 demonstrate that ceramides were not detectable using a standard TLC method in cells kept in L-serine-free-KGM, or in KGM supplemented with L-serine only, or in KGM supplemented with NAC only. Detectable ceramide levels (0.317, average peak area on densitometer) were observed only when L-serine was given to the cells in combination with NAC. The ceramide levels increased dramatically with increasing concentrations of L-serine in the presence of NAC, suggesting that the level of ceramide production depends on the dose of L-serine. Cells kept in KGM supplemented with 10 mM L-serine and 10 mM NAC made five times the amount of ceramides than the cells supplemented with 0.6 mM L-serine and 10 mM NAC.

Similar enhancement was observed when α-lipoic acid was used as the thiol compound. Table 2 illustrates the effects of α-lipoic acid in combination with L-serine on the production of epidermal ceramides in cultured human keratinocytes. The results indicate that ceramide levels were undetectable in L-serine-free-KGM medium, or in KGM supplemented with 0.1 mM α-lipoic acid alone, or in KGM supplemented with 10 mM L-serine alone. High levels of ceramides were observed only when both α-lipoic acid and L-serine were provided to the cells.

EXAMPLE 2

Enhancement of $^3$H-Serine Incorporation into Ceramide by thiols in Cultured Human Keratinocytes and Porcine Skin L-serine is the substrate of the rate-limiting reaction in the pathway of ceramide production. Incorporation of radio labeled $^3$H-L-serine into ceramides made by cultured human keratinocytes is indicative of the relative rate of ceramide production.

To study the effects of thiols on ceramide production human keratinocytes were cultured as described in Example 1. Radioisotope ($^3$H)labeled L-serine (5 JμCi/ml) was used to monitor the rate of ceramide production during the period of treatment. At the end of the incubation (24 hours), cells were harvested and lipids were extracted and separated on a standard TLC plate as described in Example 1. The separated lipids on the plates were then quantified on Bioscan, System 200 Imaging Scanner for the incorporation of $^3$H-serine into ceramides. Specific epidermal lipids were identified by comparing with the lipid standards after charring of the plate. The results that were obtained are summarized in Tables 3 and 4. Each cell in Table 3 below represents a mean of three measurements.

TABLE 3

Stimulation of Ceramide Production

| Test | H$^3$-Serine Concentration (mM) | Lipoic Acid Concentration (mM) | NAC Concentration (mM) | $^3$H-Serine Incorporation (fold increase over control) |
|---|---|---|---|---|
| A (Control) | 0 | 0 | 0 | 1.0 |
| B | 0.6 | 0 | 0 | 0.89 |
| C | 0 | 0.1 | 0 | 1.0 |
| D | 0.6 | 0.1 | 0 | 4.81* |
| E (Control) | 0 | 0 | 10 | 1.0 |
| F | 0.6 | 0 | 10 | 3.09* |

*Statistically significant increase over control

TABLE 4

Stimulation of Cerebroside Production in the Presence of L-Serine/NAC Combination

| Test | L-Serine Concentration (mM) | NAC Concentration (mM) | $^3$H-Serine Incorporation (% Total Count) |
|---|---|---|---|
| Control | 0.6 | 0 | 8.87 |
| A | 0.6 | 0.02 | 7.86 |
| B | 0.6 | 0.2 | 7.47 |
| C | 0.6 | 2.0 | 14.06 |
| D | 0.6 | 5.0 | 13.25 |
| E | 0.6 | 10.0 | 9.68 |

As indicated in Table 3, combination of α-lipoic acid (0.1 mM) and L-serine (0.6 mM) resulted in synergistic increase in $^3$H-serine incorporation into ceramide indicating an increase in the level of ceramide.

The results in Table 4 indicate that combination of L-serine with NAC results in a significant increase in cerebroside production at a level of NAC of 0.2–2 mM in vitro.

EXAMPLE 4

Enhancement of $^{14}$C-acetate Incorporation into Ceramide by thiols and S-esters in Cultured Human Keratinocytes and Porcine Skin Radioisotope labeled acetic acid, the commonly used tracer for lipid production was used to validate the effects of thiols or S-esters on ceramide production in the cultured human keratinocytes. Cells were cultured as described in Example1 and treated with α-lipoic acid or S-lactoyl-glutathione at concentrations indicated in Table 5 below. Radioisotope labeled $^{14}$C-acetate (5 μCi/ml) was used to monitor the rate of ceramide production during the period of treatment. At the end of the incubation (24 hours), cells were harvested and lipids were extracted and analyzed on a standard TLC plate as described above. The separated lipids on the plates were then quantified by Bioscan, System 200 Imaging Scanner for the incorporation of $^{14}$C-acetate into ceramides. Specific epidermal lipids were identified by comparing with the lipid standards after charring of the plate. The results that were obtained are summarized in Table 5 below. Each cell in the Table below represents a mean of three measurements.

TABLE 5

Stimulation of Ceramide Production

| Test | L-Serine Concentration (mM) | Lipoic Acid Concentration (mM) | S-Lactoyl-gutathione Concentration (mM) | $^{14}$C-Acetate Incorporation (% total counts) |
|---|---|---|---|---|
| A | 0.6 | 0 | 0 | 1.78 |
| B | 0.6 | 0 | 0 | 2.15 |
| C | 0.6 | 2.0 | 0 | 6.80* |
| D | 0.6 | 0 | 2.0 | 6.67* |

*Statistically significant increase over control (Test A)

The results in Table 5 indicate that both α-lipoic acid and s-lactoylglutathione at 2.0 mM concentration enhanced the production of ceramide more than three fold in a 24 hour period of treatment with these reagents, thus confirming the stimulatory effects of thiols and s-esters on the epidermal lipid production observed in other experiments.

EXAMPLE 5

Enhancement of $^3$H-serine Incorporation into Epidermal Ceramide in Organ Cultured Porcine Skin The stimulatory effects of thiols on epidermal lipid production were further evaluated using skin organ culture model system.

Separation of Epidermis From Dermis of Organ Cultured Skin

Organ culture of porcine skin Fresh piglet back skin (3 to 4 weeks old) was dermatomed and punch biopsies were placed dermal side down on polycarbonated insert (Costar porous 6-well dish). The biopsies were incubated in the air/liquid interface with Dulbecco's Modified Eagle Media (DMEM) at 37° C., 5% $CO_2$ until treatment. To examine the effects of thiols on epidermal lipid production in organ cultured skin, biopsies were maintained for 5 days in DMEM, and then switched to thiol-containing DMEM. $^3$H-serine (5 µCi/ml) was used to monitor the production of lipids at the 24 hour period of treatments.

Organ cultures of porcine skin were set up and maintained as described above, maintained in DMEM, 37° C., 5% $CO_2$ over 5 days and treated with 2 mM thiol-supplemented DMEM. The thiols used in this experiment include N-acetyl-L-cysteine (NAC), thiosalicylic acid (TS), thioglycerin (TG), and mercaptosuccinic acid (MSA). The treated biopsies were metabolically labeled with $^3$H-serine (5 µCi/ml) in the media for the same period as the treatment (24 hours). Epidermis of the biopsies were separated and lipids extracted as described in the methods and $^3$H-serine labeled ceramides were analyzed on Bioscan. Percent of total counts was used as a relative rate of specific epidermal lipid production.

After harvesting, epidermis of the treated biopsies were separated from dermis: Biopsies were rinsed once with PBS, and a hot (65° C.) aluminum solid column was applied directly onto the epidermis for 7 seconds. The epidermis was gently removed with a pair of fine forceps and put into glass test tubes with Teflon-lined screw caps. The epidermis was then ground and subjected to lipid analysis using lipid extraction and TLC method, as described in Example 1. Incorporation of $^3$H-serine into methanol/chloroform extractable epidermal lipids was quantified on Bioscan and percent of total counts was used as a relative rate of specific epidermal lipid production.

Each cell in the Table below represents a mean of three measurements.

TABLE 6

Effect of Thiols on Ceramide Production

| Test | L-Serine Concentration (mM) | Thiol (2 mM) | % Total Count |
|---|---|---|---|
| Control | 0.4 | None | 9.31 |
| A | 0.4 | N-acetyl-L-cysteine | 10.59 |
| B | 0.4 | Mercaptosuccinic acid | 10.90 |
| C | 0.4 | Thiosalycylic acid | 12.25* |
| D | 0.4 | Thioglycerin | 29.94* |

*Statistically significant increase over control

The results in Table 6 demonstrate that thiols enhanced the incorporation of $^3$H-serine into epidermal ceramide molecules.

EXAMPLE 6

The procedure of Example 5 was repeated except that the mass levels of ceramide were measured in stratum corneum in a non-radioisotope study. For the separation of stratum corneum, biopsies were rinsed 1× with cold PBS (phosphate-buffered saline), incubated in trypsin (0.1%) solution over night at 4° C. At the end of the incubation, whole epidermis were, removed from the dermis, suspended into 2 ml of water, and vortexed 2×. The corneum was separated from the viable epidermal cells and floating as a thin disc in the suspension. Using a pair of forceps, the corneum was transferred into a fresh test tube and was subjected to lipid extraction as described in Example 1.

The lipid extract contains two layers. The lipid was subjected to the TLC analysis as described in Example 1. The protein assay on an aqueous layer was performed as follows:

The aqueous layer of the lipid extract (as described) was dried, under nitrogen, at 37° C. 500 µl (microliters) of 0.1 N NaOH was added to the dried protein extract which was mixed well to dissolve all of the protein present. 500 µl of water was added to the extract to make the final NaOH concentration 0.05N.

50 µl aliquots of the 1 ml solution were pipetted into 96 well microtiter plates.

A series of protein standards (bovine serum albumin) was run along with the samples to create a standard curve.

Comparison of samples to standards is performed by colorimetric assay using the Pierce Micro BCA Protein Assay Reagent Kit. (Pierce, cat# 23235).

A color sensitive protein indicating solution (200 µl/well) was added to each 50 µl unknown (or standard) and, after a 30 minute incubation period, the plate was read at 570 nm on the Dynatech microtiter plate reader.

After calculating the equation of the line of the standard curve, protein content was determined by plugging in absorbance figures and solving for protein concentration. This result was multiplied by 20 (since 50 μl was taken from 1 ml) to determine the total protein content in the lipid extract's aqueous portion.)

The results that were obtained are summarized in Tables 7 and 8. Each experiment result represents a mean of the four measurements.

TABLE 7

Promotion of Ceramide Production by Lipoic Acid

| Test | L-Serine Concentration (mM) | Lipoic Acid Concentration (mM) | ng ceramide/ μg stratum corneum protein |
|---|---|---|---|
| Control | 0.4 | 0 | 0.63 |
| A | 0.4 | 0.5 | 0.53 |
| B | 0.4 | 1.0 | 1.28* |
| C | 0.4 | 2.0 | 2.29* |

*Statistically significant increase over control

TABLE 8

Promotion of Ceramide Production by N-acetyl-L-cysteine

| Test | L-Serine Concentration (mM) | N-acetyl-L-cysteine Concentration (mM) | ng ceramide/ μg stratum corneum protein |
|---|---|---|---|
| Control | 0.4 | 0 | 0.63 |
| A | 0.4 | 0.2 | 2.29* |
| B | 0.4 | 2.0 | 1.48* |

*Statistically significant increase over control

EXAMPLE 7

Example 2 was repeated except that the cells were treated with N-acetyl-L-serine and N-acetyl-L-cysteine as indicated in Table 9 below.

TABLE 9

| Test | N-acetyl-L-Serine Concentration (mM) | N-acetyl-L-cysteine concentration (mM) | $^3$H-serine incorporation (% Total Count) |
|---|---|---|---|
| A | 0 | 0 | 1.51 |
| B | 0 | 10 | 2.05 |
| C | 0.6 | 0 | 1.63 |
| D | 0.6 | 10 | 4.42* |

*Statistically significant increase over control

The results in Table 9 indicate that the combination of N-acetyl-L-serine with N-acetyl-L-cysteine results in a synergistic increase in ceramide production.

EXAMPLE 8

The following composition is a typical composition within the scope of the invention.

| | % w/w |
|---|---|
| L-serine | 5 |
| Fully hydrogenated coconut oil | 3.9 |
| N-acetyl cysteine | 0.1 |
| Brij 92* | 5 |
| Bentone 38 | 0.5 |

-continued

| | % w/w |
|---|---|
| Preservative | 0.3 |
| MgSO$_4$7H$_2$O | 0.3 |
| Butyrated hydroxy toluene | 0.01 |
| Perfume | qs |
| Water | to 100 |

*Brij 92 is polyoxyethylene (2) oleyl ether

EXAMPLE 9

This example illustrates an oil-in-water cream incorporating the inventive composition.

| | % w/w |
|---|---|
| N-acetyl serine | 5 |
| Fully hydrogenated coconut oil | 3.9 |
| α-Lipoic acid | 0.1 |
| Brij 92* | 5 |
| Bentone 38 | 0.5 |
| Preservative | 0.3 |
| MgSO$_4$7H$_2$O | 0.3 |
| Butyrated hydroxy toluene | 0.01 |
| Perfume | qs |
| Water | to 100 |

*Brij 92 is polyoxyethylene (2) oleyl ether

EXAMPLE 10

This example illustrates an oil-in-water cream incorporating the inventive composition.

| | % w/w |
|---|---|
| L-serine | 10 |
| Mineral oil | 4 |
| N-acetyl cysteine | 1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 11

This example illustrates an alcoholic lotion incorporating the composition according to the invention.

| | % w/w |
|---|---|
| N-acetyl serine | 10 |
| Mineral oil | 4 |
| α-lipoic acid | 1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |

-continued

| | % w/w |
|---|---|
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 12

This example illustrates an alcoholic lotion incorporating the composition according to the invention.

| | % w/w |
|---|---|
| L-serine | 1 |
| N-acetyl cysteine | 0.2 |
| Ethanol | 40 |
| Perfume | qs |
| Butylated hydroxy toluene | 0.01 |
| Water | to 100 |

EXAMPLE 13

This example illustrates another alcoholic lotion containing the inventive composition.

| | % w/w |
|---|---|
| N-acetyl-L-serine | 1 |
| N-acetyl cysteine | 0.2 |
| Dimethylsulphoxide | 10 |
| Ethanol | 40 |
| Antioxidant | 0.1 |
| Perfume | qs |
| Water | to 100 |

| | % w/w |
|---|---|
| N-acetyl serine | 1 |
| α-lipoic acid | 0.2 |
| Ethanol | 40 |
| Perfume | qs |
| Butylated hydroxy toluene | 0.01 |
| Water | to 100 |

EXAMPLE 14

This example illustrates another alcohol lotion containing the inventive composition.

| | % w/w |
|---|---|
| Thiolactic acid | 1 |
| N-acetyl-serine | 0.2 |
| Dimethylsulphoxide | 10 |
| Ethanol | 40 |
| Antioxidant | 0.1 |
| Perfume | qs |
| Water | to 100 |

EXAMPLE 15

This example illustrates a suncare cream incorporating the lipid enhancement system of the invention:

| | % w/w |
|---|---|
| L-serine | 5 |
| N-acetyl Cysteine | 1 |
| Ceramide-1 | 0.01 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 16

This example illustrates a suncare cream incorporating the lipid enhancement system of the invention:

| | % w/w |
|---|---|
| N-acetyl serine | 5 |
| α-lipoic acid | 1 |
| Ceramide-1 | 0.01 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 17

This example illustrates a non-aqueous skin care composition incorporating the inventive combination.

| | % w/w |
|---|---|
| L-serine | 5 |
| N-acetyl cysteine | 0.1 |
| Silicone gum SE-30[1] | 10 |
| Silicone fluid 345[2] | 20 |
| Silicone fluid 344[3] | 55.79 |
| Squalene | 10 |
| Ceramides | 0.01 |
| Linoleic acid | 0.01 |
| Cholesterol | 0.03 |
| 2-hydroxy-n-octanoic acid | 0.7 |
| Vitamin A palmitate | 0.5 |
| Vitamin E linoleate | 0.5 |
| Herbal oil | 0.5 |
| Ethanol | 2 |

[1] A dimethyl silicone polymer having a molecular weight of at least 50,000 and a viscosity of at least 10,000 centistokes at 25° C., available from GEC

[2] Dimethyl siloxane cyclic pentamer, available from Dow Corning Corp.

[3] Dimethyl siloxane tetramer, available from Dow Corning Corp.

EXAMPLE 18

This example illustrates a non-aqueous skin care composition incorporating the inventive combination.

|  | % w/w |
|---|---|
| N-acetyl serine | 5 |
| α-lipoic acid | 0.1 |
| Silicone gum SE-30[1] | 10 |
| Silicone fluid 345[2] | 20 |
| Silicone fluid 344[3] | 55.79 |
| Squalene | 10 |
| Ceramides | 0.01 |
| Linoleic acid | 0.01 |
| Cholesterol | 0.03 |
| 2-hydroxy-n-octanoic acid | 0.7 |
| Vitamin A palmitate | 0.5 |
| Vitamin E linoleate | 0.5 |
| Herbal oil | 0.5 |
| Ethanol | 2 |

[1] A dimethyl silicone polymer having a molecular weight of at least 50,000 and a viscosity of at least 10,000 centistokes at 25° C., available from GEC

[2] Dimethyl siloxane cyclic pentamer, available from Dow Corning Corp.

[3] Dimethyl siloxane tetramer, available from Dow Corning Corp.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin treatment composition for enhancing ceramide production in keratinocytes consisting essentially of:
   (i) from about 0.0001% to about 50% of an ingredient selected from the group consisting of L-serine, N-acetyl-L-serine and mixtures thereof;
   (ii) from about 0.0001% to about 50% of an ingredient selected from the group consisting of N-acetyl-cysteine, α-lipoic acid and mixtures thereof; and
   (iii) a cosmetically acceptable vehicle.

2. The composition of claim 1 wherein the amount of ingredient (i) is at least 0.01%.

3. The composition of claim 1 wherein the amount of ingredient (ii) is from about 0.01% to about 20% by weight of the composition.

4. The composition of claim 1 wherein ingredient (i) is N-acetyl serine and ingredient (ii) is α-lipoic acid.

5. The composition of claim 1 wherein ingredient (i) is selected from the group consisting of serine and N-acetyl serine, and ingredient (ii) is N-acetyl-cysteine.

6. A method of enhancing the production of ceramide in keratinocytes, the method comprising applying topically to the skin the composition comprising:
   (i) from about 0.0001% to about 50% of an ingredient selected from the group consisting of L-serine, N-acetyl-L-serine and mixtures thereof;
   (ii) from about 0.0001% to about 50% of an ingredient selected from the group consisting of N-acetyl-cysteine, α-lipoic acid, S-lactoyl-glutathione and mixtures thereof; and
   (iii) a cosmetically acceptable vehicle.

7. The method of claim 6 wherein the amount of ingredient (i) is at least 0.01%.

8. The method of claim 6 wherein the amount of ingredient (ii) is from about 0.01% to about 20% by weight of the composition.

9. The method of claim 6 wherein ingredient (i) is N-acetyl serine and ingredient (ii) is α-lipoic acid.

10. The method of claim 6 wherein ingredient (i) is selected from the group consisting of serine and N-acetyl serine, and ingredient (ii) is N-acetyl-cysteine.

* * * * *